(12) United States Patent
Odriozola Orlandi

(10) Patent No.: US 10,376,204 B2
(45) Date of Patent: Aug. 13, 2019

(54) DEVICE AND METHOD FOR ASSESSING THERMOALGESIC AND VIBRATORY SENSITIVITY

(76) Inventor: Ariel Andres Odriozola Orlandi, Barcelona (ES)

( * ) Notice: Subject to any disclaimer, the term of this patent is extended or adjusted under 35 U.S.C. 154(b) by 407 days.

(21) Appl. No.: 13/262,126

(22) PCT Filed: Mar. 16, 2010

(86) PCT No.: PCT/ES2010/070155
§ 371 (c)(1),
(2), (4) Date: Nov. 28, 2011

(87) PCT Pub. No.: WO2010/112647
PCT Pub. Date: Oct. 7, 2010

(65) Prior Publication Data
US 2012/0109003 A1    May 3, 2012

(30) Foreign Application Priority Data

Apr. 1, 2009 (ES) .................................. 200900890

(51) Int. Cl.
*A61B 5/00* (2006.01)

(52) U.S. Cl.
CPC .......... *A61B 5/4827* (2013.01); *A61B 5/0051* (2013.01); *A61B 5/483* (2013.01); *A61B 5/0024* (2013.01); *A61B 5/7475* (2013.01)

(58) Field of Classification Search
CPC ................. A61B 5/4824–5/483; A61B 5/0051
USPC ................................................ 600/552–555
See application file for complete search history.

(56) References Cited

U.S. PATENT DOCUMENTS

| 2,908,268 A * | 10/1959 | Guest ....................... A61B 9/00 600/552 |
| 5,022,407 A | 6/1991 | Horch et al. |
| 5,897,510 A * | 4/1999 | Keller et al. .................. 600/594 |
| 2009/0082694 A1* | 3/2009 | Poisner ................ A61B 5/0051 600/552 |
| 2011/0112431 A1* | 5/2011 | Golosarsky .......... A61B 5/0051 600/552 |

FOREIGN PATENT DOCUMENTS

| EP | 2012427 | 1/2009 |
| JP | 2005-052598 | 3/2005 |
| WO | WO 2010/112647 | 10/2010 |

OTHER PUBLICATIONS

Examination Report dated Mar. 4, 2015 From the Instituto Mexicano de la Propiedad Industrial, IMPI Re. Application No. MX/a/2011/010226.
(Continued)

*Primary Examiner* — Devin B Henson
*Assistant Examiner* — H. Q. Nguyen

(57) ABSTRACT

The invention relates to a device for assessing thermoalgesic and vibratory sensitivity, including a first unit (1) configured to apply, to localized points of the patient, a plurality of stimuli comprising vibrations and temperature changes, a second unit (2) for gathering data communicating with the first unit, wherein the communication between the first unit (1) and the second unit (2) takes place by means of a two-way wireless transmission means. The invention also relates to a method for assessing vibratory, thermal and thermoalgesic sensitivity using the device according to the invention.

12 Claims, 12 Drawing Sheets

(56) References Cited

OTHER PUBLICATIONS

International Preliminary Report on Patentability dated Jan. 26, 2011 From the International Preliminary Examining Authority Re. Application No. PCT/ES2010/070155 and Its Translation Into English.
Notice of the Result of Substantive Examination Pursuant to Article 52(1) of Patent Law No. 14/2001 Dated Apr. 23, 2014 From the Ministry of Law and Human Right of the Republic of Indonesia, Directorate General of Intellectual Property Rights, Patent Directorate Re. Application No. W-00201103520 and Its Translation Into English.
Notification of Office Action and Search Report dated Jul. 4, 2013 From the State Intellectual Property Office of the People's Republic of China Re. Application No. 201080020110.4 and Its Translation of Office Action Into English.
Office Action dated Apr. 15, 2015 From the Israel Patent Office Re. Application No. 215496 and Its Translation Into English.
Patent Examination Report dated May 5, 2015 From the Australian Government, IP Australia Re. Application No. 2010230108.
Request for Examination dated Mar. 24, 2014 From the Rospatent, Federal Government Institution, Federal Institute of Industrial Property of the Federal Service for Intellectual Property, Patents and Trademarks of the Russian Federation Re. Application No. 2011144104 and Its Translation Into English.
Requisition by the Examiner dated Feb. 17, 2016 From the Canadian Intellectual Property Office Re. Application No. 2,757,312.
Search Report dated May 3, 2013 From the Intellectual Property Office of Singapore Issued by the Hungarian Intellectual Property Office Re. Application No. 201107152-9.
Supplementary European Search Report dated Apr. 24, 2014 From the European Patent Office Re. Application No. 10758093.

\* cited by examiner

FIG. 12
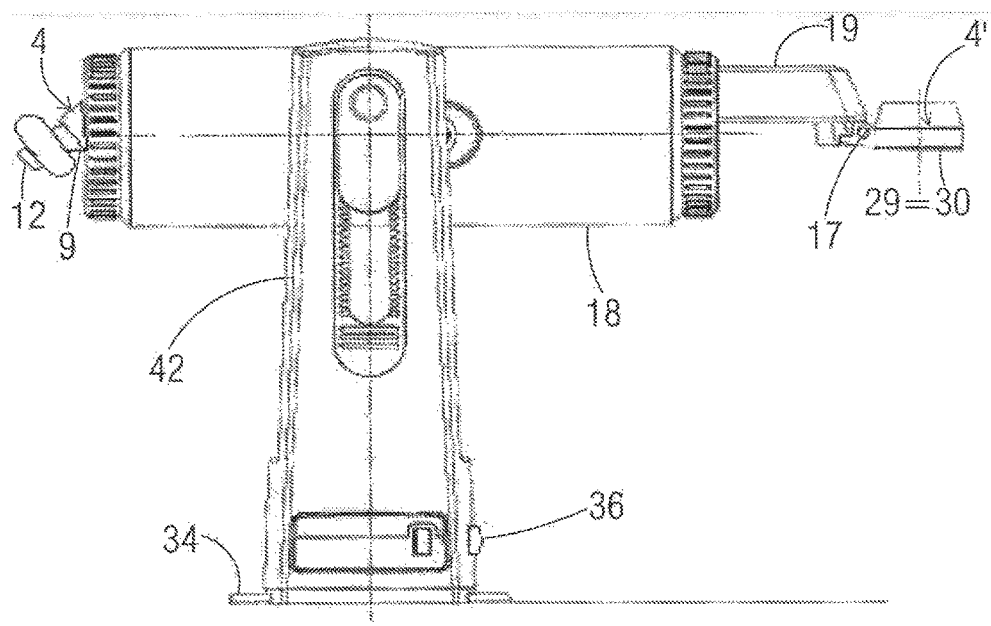
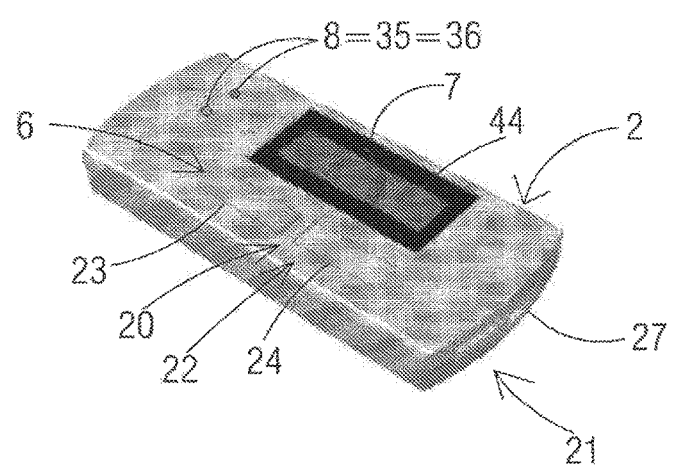
FIG. 13

DEVICE AND METHOD FOR ASSESSING THERMOALGESIC AND VIBRATORY SENSITIVITY

DESCRIPTIVE MEMORY

Object of the Invention

The present invention patent application is comprised within the field of medicine and more specifically within the field of the assessment of the thermoalgesic and vibratory sensitivity for the diagnosis and/or monitoring of diseases such as sensitive neuropathy, which registers the functional status of peripheral sensitive nerve fibres.

Background of the Invention

At present no appropriate devices are known for the rapid self-monitoring of the magnitude of sensitive loss as an indicator of the risk of foot ulceration, which are different from the ideal apparatus for the detection of subclinical changes in patients with a condition leading to neuropathy but that are still asymptomatic.

Distal sensitive neuropathy of the four limbs is present in multiple diseases with symptoms and/or signs that make up an initial presentation of the condition or as a consequence of complications of the base disease and/or the treatments thereof. Diabetes mellitus type 1, type 2; B1, B6 and B12 hypovitaminoses; malnutrition; leprosy; amyloidosis; vasculitis; collagen diseases; AIDS; Pierre-Marie-Toth disease; paraneoplasic diseases; post-chemotherapy; compressive radiculopathies; Friedrich's ataxia; hereditary motor-sensitive neuropathy type 1; Tangier's disease . . . .

The clinical evaluation of sensitivity plays an important role during the neurological examination. By using simple methods with hand-held tools (disposable needles, brushes and/or cotton, glass tubes with hot or cold water, a 248-Hz tuning fork, a qualitative guide, . . . ), examiners evaluate whether sensitivity is preserved or not. The examiner uses the comparative method on explored areas to identify differences between those that have been affected and those that have not.

Current diagnostic methods for sensitive impairment are semi-quantitative. They include tests for assessment on nerve fibres of heat, cold, vibration and thermal pain.

The tool equipment is based on thermal, thermoalgesic and vibratory stimulant devices, which are under the operation of a software programme that regulates stimulation, as well as a processor of the response conveyed by the patient that is being examined.

Specifically, Thermotest methods are used to assess the function of afferent pathways related to the sensitive submodalities of small-diameter fibres. It is an exploration method in which a temperature increase or decrease ramp is applied and the sensation thresholds are collected for the specific sensation, such as heat, cold or pain. As for the vibratory methods, these are used to assess the function status of medium-sized afferent nerve fibres that are sensitive to vibration differences.

Several programmes are used for forced-response choice, the yes/no paradigm and the yes/no response with a visual graded scale.

The complexity of each of these tools requires, for its diagnostic development, of sophisticated knowledge about software and medicine; hence they are conducted by medical staff who are specialized in this type of diseases (neurophysiologists).

The tool equipment is large in size (not portable), slow in test development (average time: 1.5 to 2 hours) and requires complex interpretations of its output and provides difficult-to-understand results; electrical installation is complex, with test calibrations requiring infrared thermometers, laser calibrators of distance and with great disadvantages when transporting it derived from its large size, installation and decalibration.

Some workers use a container with about 7 liters of water containing a disinfectant, from which the fluid is emitted through a system of 2 refrigerant hoses towards a large-sized Peltier plate, to allow its heating and cooling. In addition to a complex vibratory system composed of an engine arranged in a 800-g box with a 300-g sand cushion, a calibration system with a laser situated at a distance of 4 m and an alternator plus a computer connected to a box with the electronics of the Thermotest. Other elements are a number of boxes including pedalboards for both hands and/or feet with a vibration regulator, through an engine and connected to a data processor.

All the above said prevents implementation as a diagnostic approach method for quick and simple daily use in the clinic and/or as a monitoring test for non-medical healthcare personnel or for the patients themselves.

Other types of device for this kind of diagnostic test have the same characteristics than those described above and also carry out only one of the tests on the nerve fibre. The cost of this equipment is extremely high, as are the replacement parts, and also requires the continuous calibration for its maintenance. The prices of the various apparatus ranges between 6,000 and 24,000 euros. This situation impairs the required capacity for early detection of diseases allowing potential early treatment, and impairing its potential for determining the indicated treatments, worsening the condition and its extremely serious consequences, which imply high health costs.

Because of all the above, the need has been identified of a device that can help to prevent the unchecked progress of neuropathies and provide a strong early indicator of risk of neuropathy on feet.

Said device can be used routinely by patients and/or healthcare personnel without prior health knowledge, with an aim to carrying out in a rapid manner a "Self-screen" for the early detection of distal sensitive perception impairment in each area explored when exposed to stimuli with different thresholds that have been pre-established from standard values of vibration, heat, cold and thermoalgesic pain.

This objective is achieved by the invention as defined in claim 1; the preferred embodiments of the invention are defined in the dependent claims.

DESCRIPTION OF THE INVENTION

The present invention relates to a device for assessing thermoalgesic and vibratory sensitivity, including: a first unit configured to apply a plurality of stimuli comprising vibrations and temperature changes, a second unit for gathering data that communicates with the first unit and has the option of communicating with a PC.

The device is characterized in that the first unit comprises: an outer casing, physical means for generating vibrations and physical means for generating cold-heat, both configured to act directly on the patient, which are arranged inside the outer casing, moving linearly with respect to the casing in order to deploy from it, making a turn around it at the moment when the stimulus is applied, and on/off and control means configured to activate the first unit and to vary the intensity of both vibrations and temperature.

On the other hand, the second unit comprises: data input means, data display means and means for indicating the different stages of operation of the first unit.

In addition, the communication between the first unit and the second unit takes place by means of a two-way wireless transmission means Thus, thanks to the particular configuration described for the device, a quick and simple monitoring is achieved for assessing the vibratory and thermoalgesic sensitivity of a patient affected by sensitive neuropathy, registering the functional status of the peripheral sensitive nerve fibres.

The vibration generating means of the first unit may comprise: a tuning fork that has two arms converging on a central point, from which point an arm applying the vibrations projects, the end of which has a polyvinyl or Teflon button, the arm forming an angle of application of 30° with respect to the main axis of the first unit. Said applicator is connected to the outer casing of the first unit through a rubber washer and to the free end of each arm, a piezo-electrical system or a speaker with an inner coil generating vibrations is optionally fixed, the cables of the vibration generating means running through the central part of the first unit casing.

On the other hand, the means generating cold-heat of the first unit may comprise a Peltier cell with ventilators that will be rotatably connected according to an axis that is perpendicular to the turning axis of the casing, to an ejector arm that is parallel to said turning axis. Said arm is connected to the casing so it can move linearly with respect to it according to a direction parallel to the rotating axis, in such a way that, in the retracted position of the means that generate cold-heat, the Peltier cell with ventilators will be situated in parallel to the arm and in a deployed position the arm will protrude from the casing, and once extracted from it, the Peltier cell with ventilators will be able to rotate around the axis of the arm's end, adopting a certain tilt with respect to the axis of the casing.

The casing of the first unit can be tubular, of circular outline and can be made of a material of great hardness and resistance. On the tips it has a rubber washer, which dampens the impact in case of fall, and on the centre and ends is the rotation device, which is of the same material and has a power button for the first unit.

The means for data introduction of the second unit may comprise a button pad that is divided in two areas, a first area with a power button, and another area with two buttons for the input of data corresponding to the vibration generating means and for the input of data corresponding to the means generating cold-heat. The second area of buttons may comprise a first button that will be pushed when the patient identifies the vibration, and a second button that will be pushed when the patient identifies none.

The communication between the first unit and the second unit can take place by means of radiofrequency or infrared radiation, and alternative transmission means can be used allowing the bidirectional communication between the first and second units.

The first unit may comprise a skin temperature sensor and an ambient temperature sensor that will determine the coordinates of temperature to be able to carry out the assessment.

Additionally, the first unit may be coupled to the second unit through a slot made in the second unit (2) and a projection fitting into said slot, associated to the first unit, in such a way that both units are interconnected with each other, forming the device.

The first and second units may be powered through at least a rechargeable battery, which in the case of the first unit is located in one of its bases. The first unit may comprise on one of its bases, which rests on the ground during the use of the device, a rubber layer to prevent the transmission of vibrations from the ground to the arm of the vibration generating means, with an aim to said vibrations from the ground not being perceived by the patient and therefore, so they do not interfere with the assessment of vibration sensitivity.

The second unit may comprise visual and sound means of warning configured to indicate the end of the battery charge and may also have a port for communicating said second unit to a personal computer.

The indicator means of the second unit may comprise a plurality of different-colour leds, configured to light up when the vibration generating and cold-heat means are on.

Finally, the means for data display of the second unit may comprise a screen located next to the first and second areas of buttons of the button pad, configured to display at least the following data: the date and time, the number and type of test being run, the score obtained in each test and in total, and the percentage of stimuli detected by the patient.

A second important aspect of the invention envisages a procedure for using the device and for assessing the sensitivity of the patient. Said procedure involves the following steps:

a).—switching on the first and second units b).—implementation of a self-test by the first and second units, of at least the following parameters: battery charge, ambient temperature, skin temperature and radiofrequency or infrared communication status.

c).—deployment of the vibration applicator from one of the ends of the first unit casing.

d).—placement of the end of the vibration applicator on a localized area of the nail bed skin of the first toe of the right foot, continuing with the second toe until completing the foot, then continuing with the left foot and subsequently with the upper limbs.

e) placement under the ball of each explored finger of an insulating rubber plate.

f).—application of a plurality of vibrations of different intensity on each finger, said application being alternating within a limited period of time.

g).—pulsation by the patient, for each of the different vibrations, of the first button of the second unit if the vibration is felt, and of the second button of said unit if nothing is felt.

h).—quantification by the second unit of the percentage of vibrations detected by the patient, to determine a degree of sensitivity.

i).—deployment of the Peltier cell with ventilators from one of the ends of the casing of the first unit.

j).—placement of one of the sides of the Peltier cell with ventilators on the localized area of the skin of the back of the right foot, continuing with the left foot and subsequently with the upper limbs.

k).—application of a plurality of cold-heat stimuli to each limb, said application being alternating within a limited period of time.

l).—pulsation by the patient, for each of the different cold-heat/pain stimuli, of the first button if the stimulus is positively felt, or of the second button if it is not felt, after each stimulus.

m).—quantification by the second unit of the percentage of changes of temperature and pain induced by cold-heat correctly detected by the person, to determine a degree of sensitivity.

Considering the characteristics of the device for assessing the vibratory, thermal and thermoalgesic sensitivity object of the present invention, said device has the following advantages:

1. Compact size and light weight in more than 75% of existing devices (portable).
2.—Integration in a single unit for the assessment of the 4 tests in less than 15 minutes, with evaluation of small and medium-sized sensitive fibres using the same device.
3.—Absence of: replacement liquid coolants, manual controllers of liquids temperature, use of antiseptics for liquids.
4.—Simple-to-use software for a user without computer-specific and/or medical/health-related knowledge.
5.—Autonomy by rechargeable battery/non-rechargeable batteries.
6.—Reduced cost of device and tests.
7.—Instantaneous delivery of semi-quantitative/quantitative results with an interpretation for non-medical professionals.
8.—It allows the systematic self-monitoring of alterations and/or normality.
9.—Results response in visual and/or aural form for persons with visual deficit.
12.—Dispenses with the use of a PC, which is used in a supplementary, not compulsory, way.
13.—Applicable to all body surfaces.

BRIEF DESCRIPTION OF THE DESIGNS

In FIG. 2b a lateral perspective view of said device is represented.

DESCRIPTION OF A PREFERRED EMBODIMENT

Figure 1:
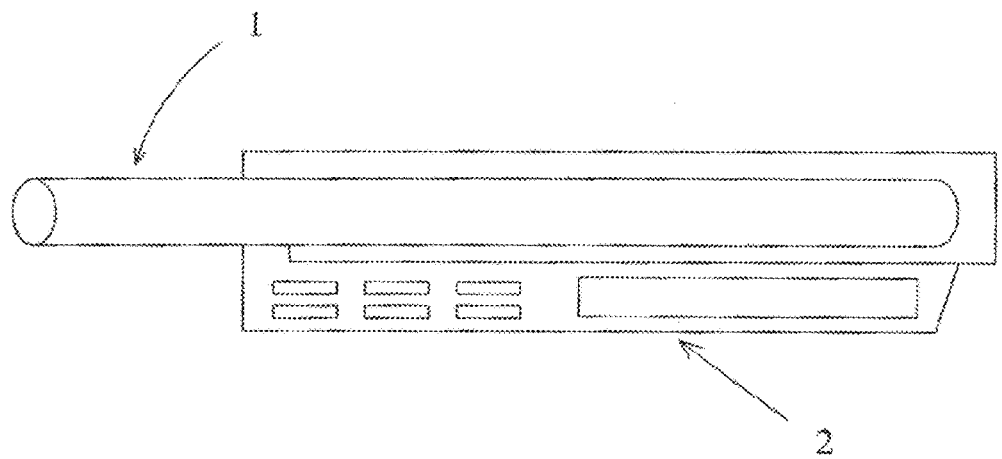
FIG. 1 represents a view of the device integrating the first and second units.
Figure 2:
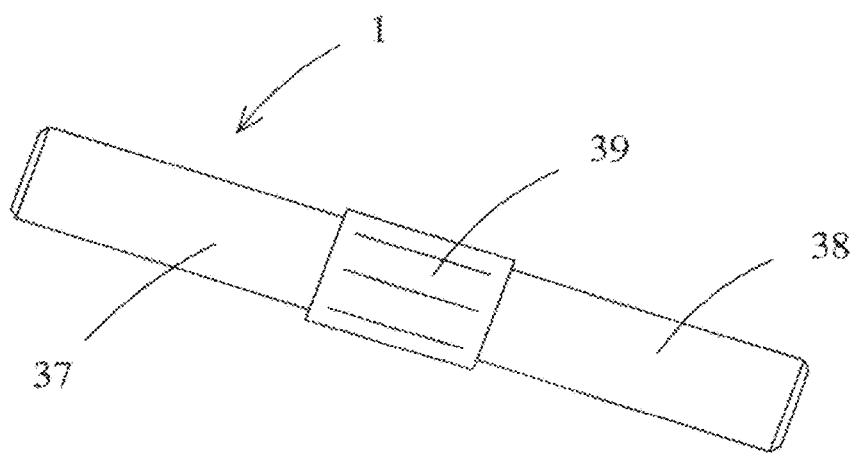
FIG. 2 represents a perspective front view of the device integrating the first unit for assessing sensitivity, object of the present invention, said first unit being in retracted position.

As can be seen in FIG. 1, the device for assessing the vibratory and thermoalgesic sensitivity, object of the present invention, is essentially made up of a first unit (1) and a second unit (2) that, when the device is being used, are mutually integrated thanks to a slot made in the second unit (2) and a protrusion or projection fitting perfectly inside said slot, said projection being made in the first unit (1).

The first unit (1) is made up of an outer casing (3) with a cylindrical configuration and that is divided into two parts (37) and (38), this unit having a sleeve on each of the two ends or a single sleeve (39) between the two parts, whereby thanks to a relative turn of both parts of the first unit (1) a vibration generating means (4) or a means generating cold-heat (4'), or both simultaneously if necessary, may be deployed.

Figure 3:
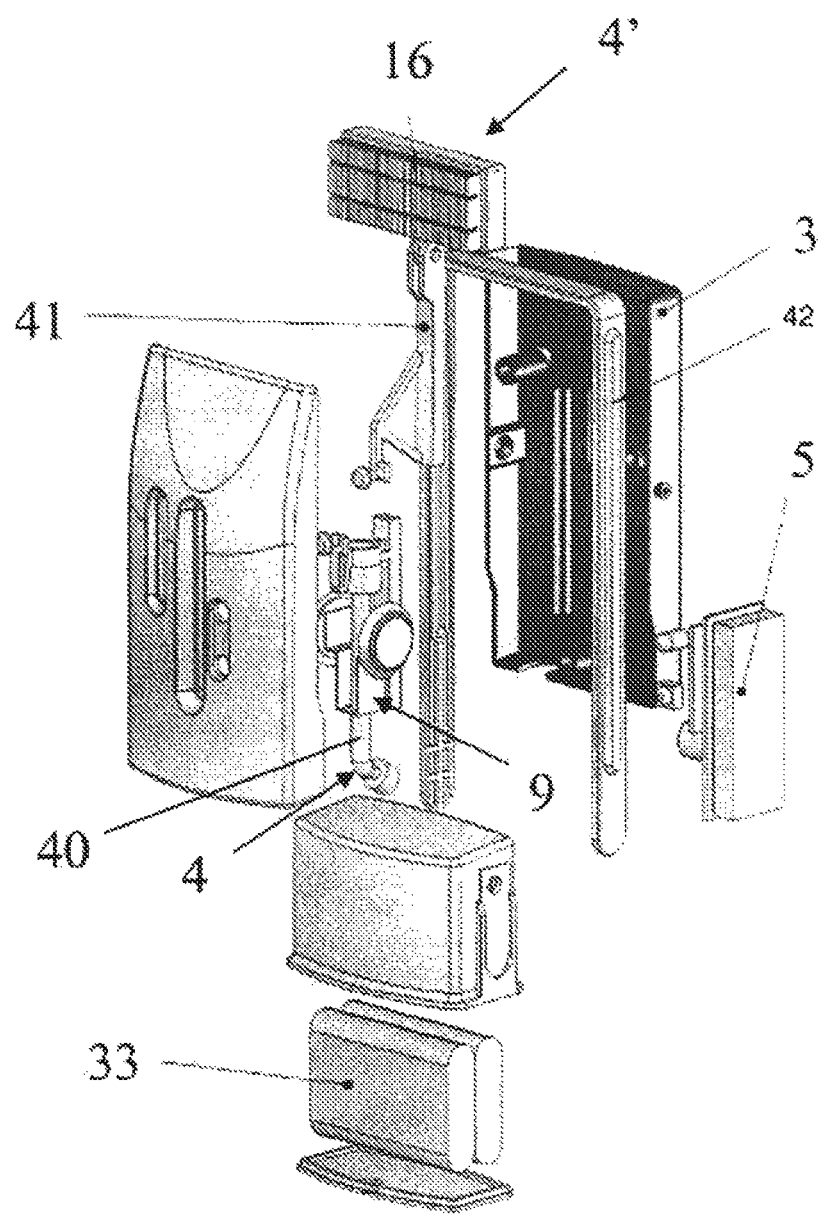
FIG. 3 represents a perspective view of the first unit in deployed position.

In FIG. 3 the constitution of the first unit (1) is detailed, which in addition to the mentioned stimuli-generating means (4) and (4'), includes on/off and control (5) means, whose mission is, on one hand, to allow the switching on and off of the first unit (1) and, on the other hand, to control by means of an electrical circuit (5') the intensity of the stimuli applied to the patient, both vibrations and cold-heat.

Figure 7:
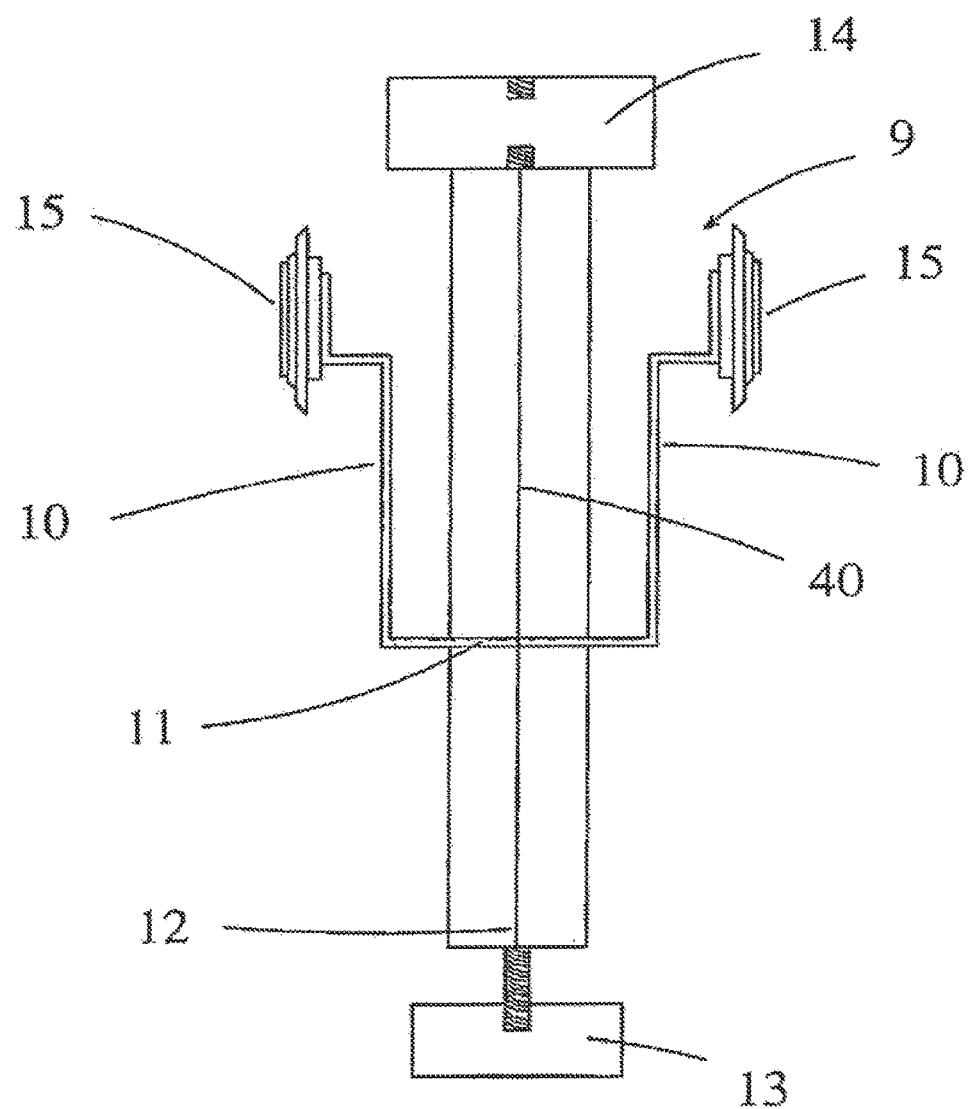
FIG. 7 represents a perspective view of the vibration generating means forming part of the first unit of the device.
Figure 8:
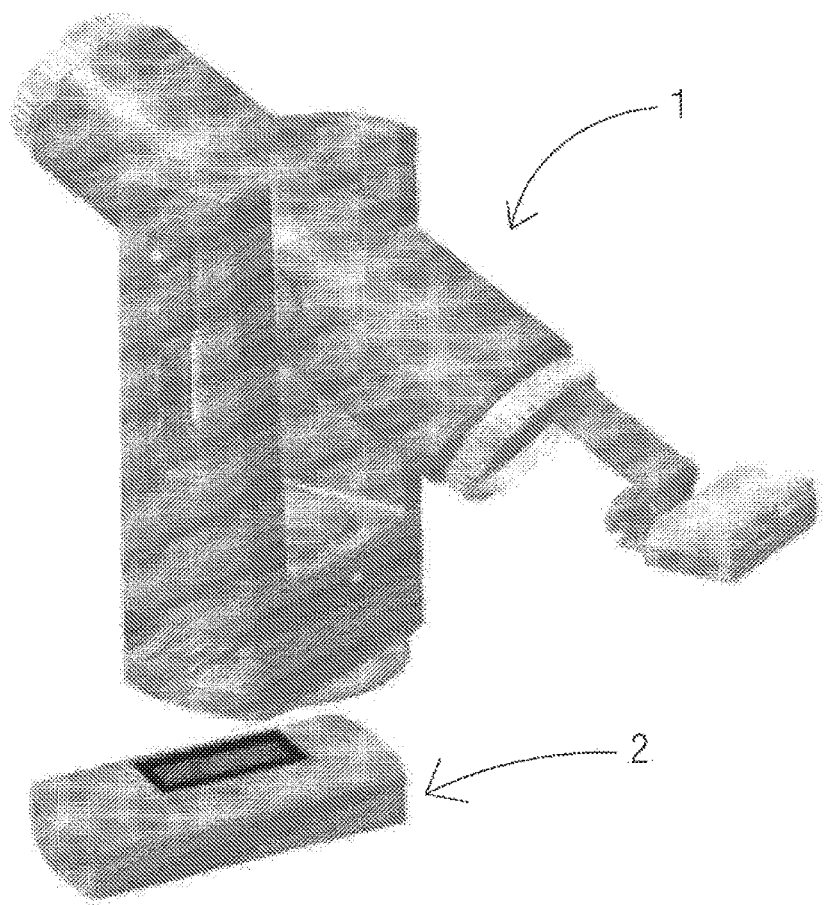
Figure 9:
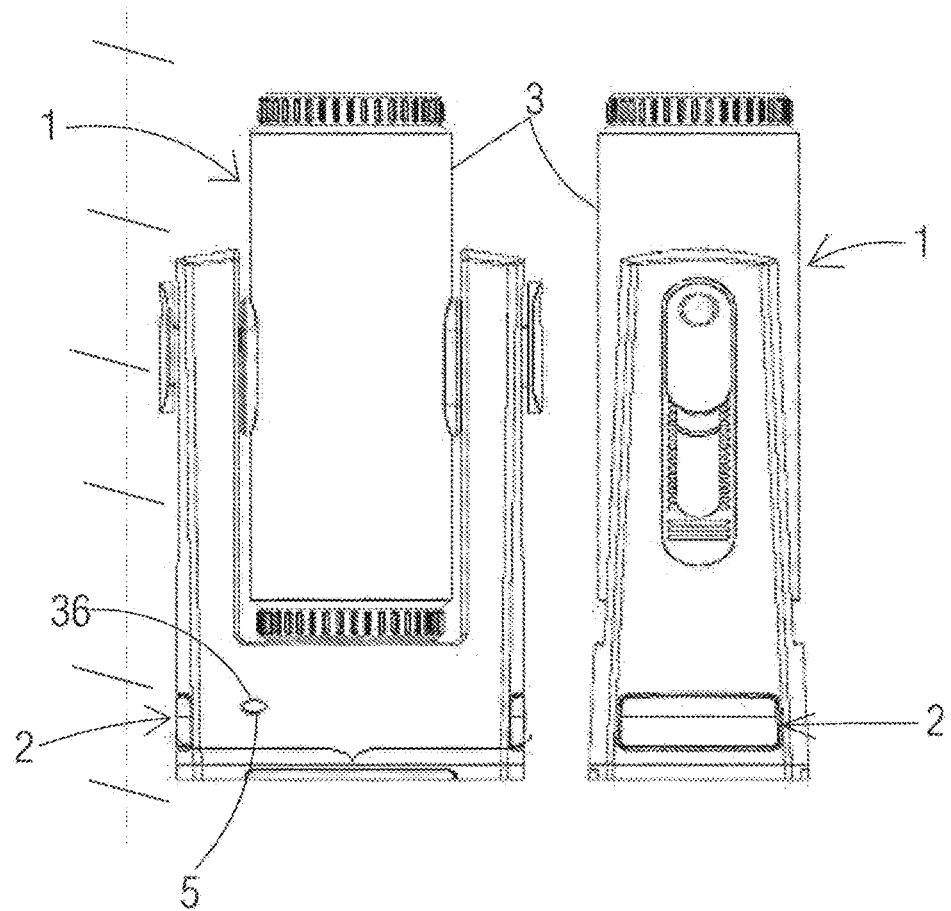
Figure 10:
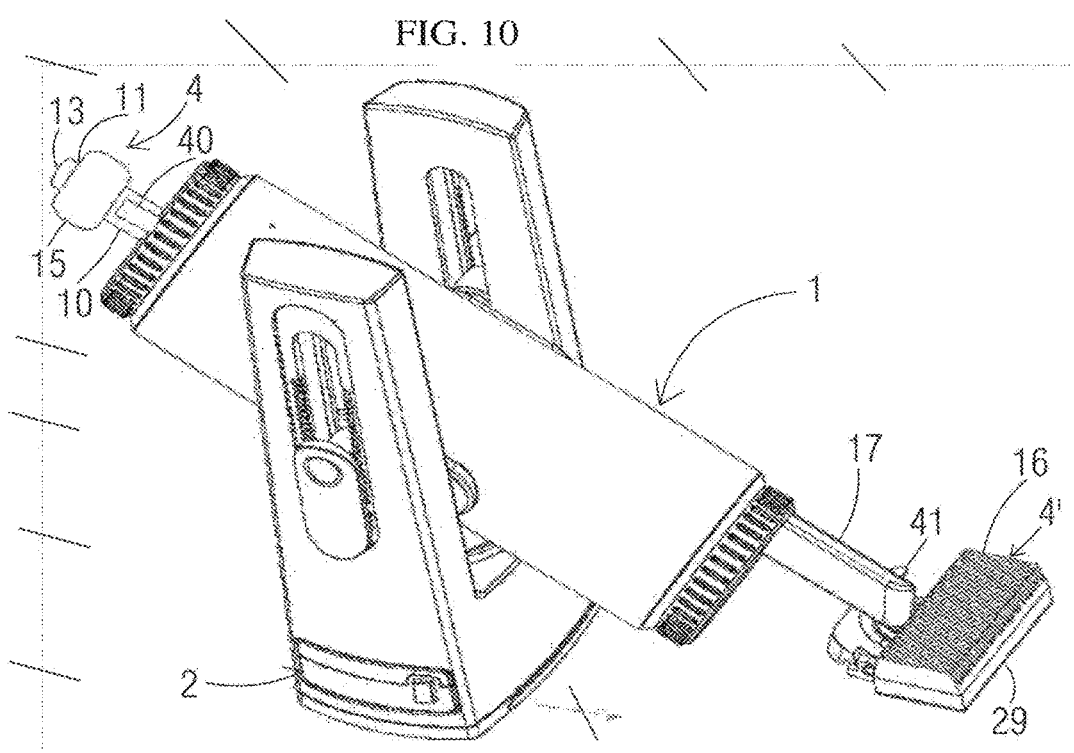
Figure 11:
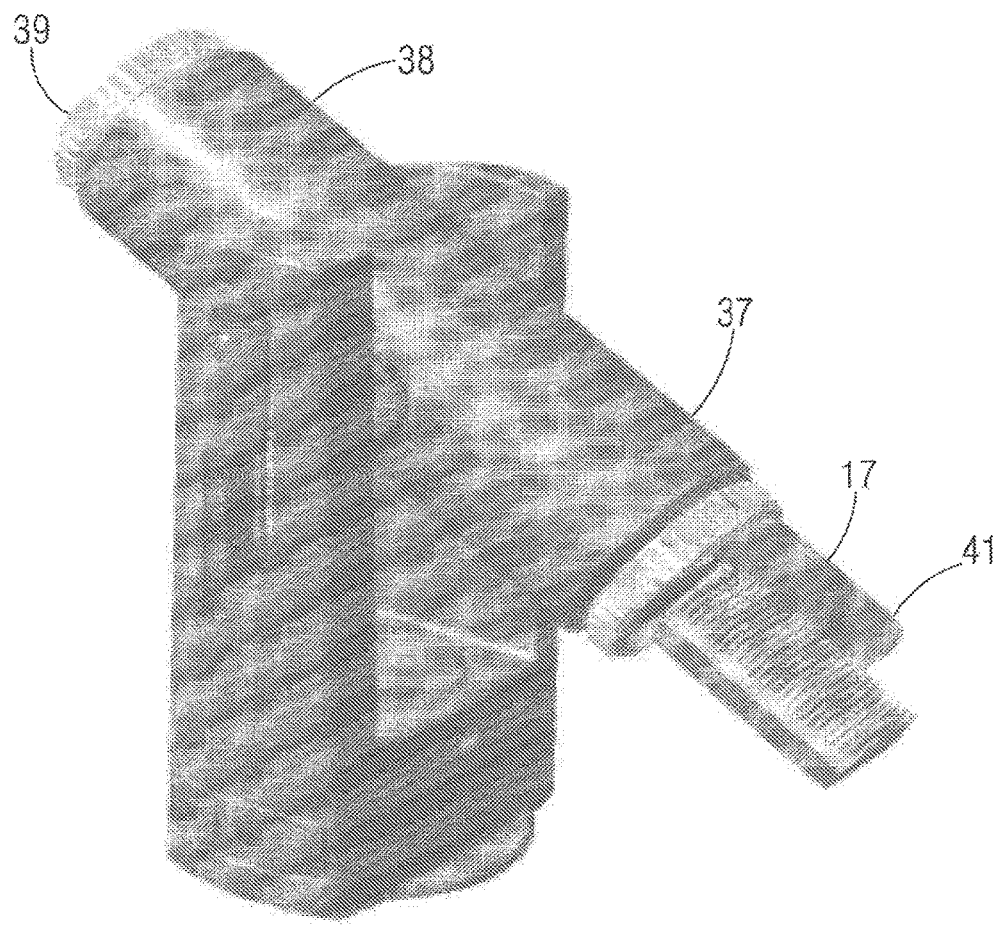
Figure 14:
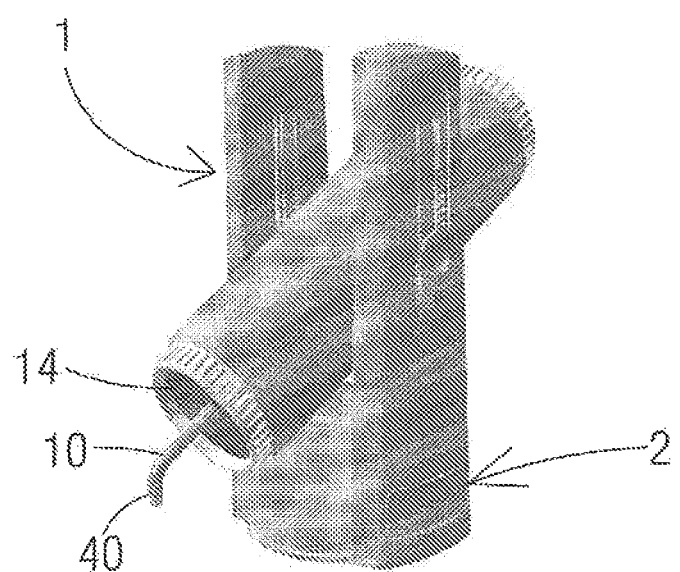

The vibration generating means (4) comprise a tuning fork (9), represented in detail in FIG. 7, which consists of arms (10) that converge on a central point (11) crossed by a stem (40) that makes up the vibration applicator (12), which has in its free end a Teflon button (13). In the connection area between said applicator (12) and the casing (3) is a rubber washer (14) to prevent the leakage of vibrations. On each end of the arms (10) the corresponding piezo-electric elements (248-125 Hz) or speakers that have an inner coil are arranged, which are responsible for generating the vibration, as they emit a vibratory discharge through the changes experienced by the piezo-electric unit in response to the electrical stimulus of this element, or through sound generating a vibratory effect in conjunction with the coil and with a frequency phase shift of 180°, leading to transmission through the arms of the tuning fork (9) to the applicator (12). The energy feeding the first unit (1), which is destined to said vibration generating means (4), is of 9 V, maintaining a vibration with a sinusoidal wave form of 4 milliseconds duration.

The vibration generating means (4) may be optionally displaced linearly with respect to the casing (3), being deployed from it through activation of the sleeve (39), enabling the means in the inside of the first unit that are appropriate for achieving said displacement.

For example, guides may be enabled (41).

Figure 4:
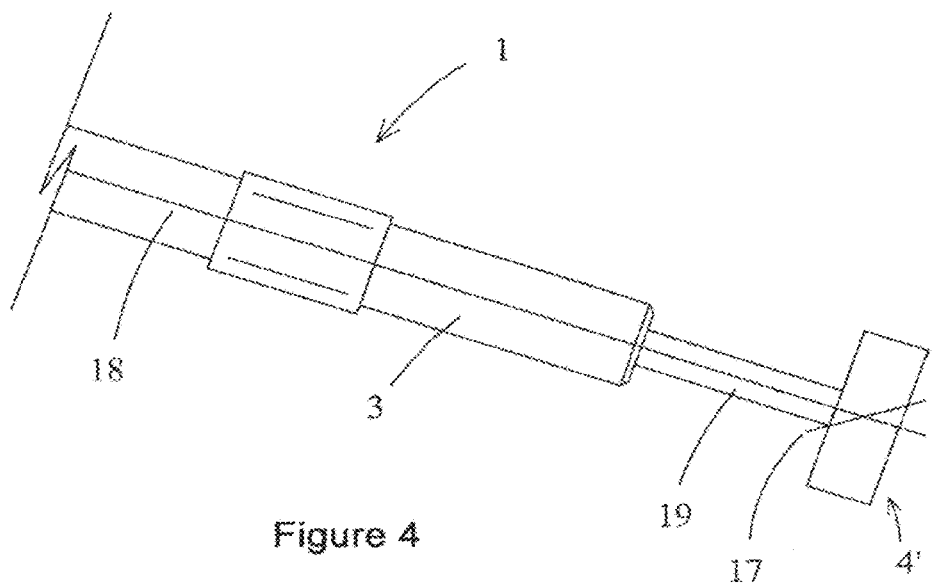
FIG. 4 represents a perspective view of the first unit forming part of the device for assessing sensitivity, object of the present invention, said first unit being in partly deployed position.

On the other hand, the means generating cold-heat (4') have a Peltier cell with ventilators (16), in particular a Peltier thermode with ventilators, which is arranged on the end of an ejector arm (19), in parallel to the turning axis (18) of the casing (3), being rotatable with respect to said arm (19) according to an axis (17) perpendicular to the turning axis (18). In this way, in the idle state of the first unit (1), the casing contains a Peltier cell with ventilators (16) that by turning the sleeve (39) is extracted from the casing (3) projecting the arm (19), on the end of which the cell (16) lies in retracted position, because the diameter of the casing (3) is smaller than the necessary width for the Peltier cell with ventilators, as can be seen in FIG. 4. To be able to use the cell (16), it is retracted with respect to the arm's end (19) according to the rotational axis (17), resulting in it being completely deployed and ready for use.

Figure 5:
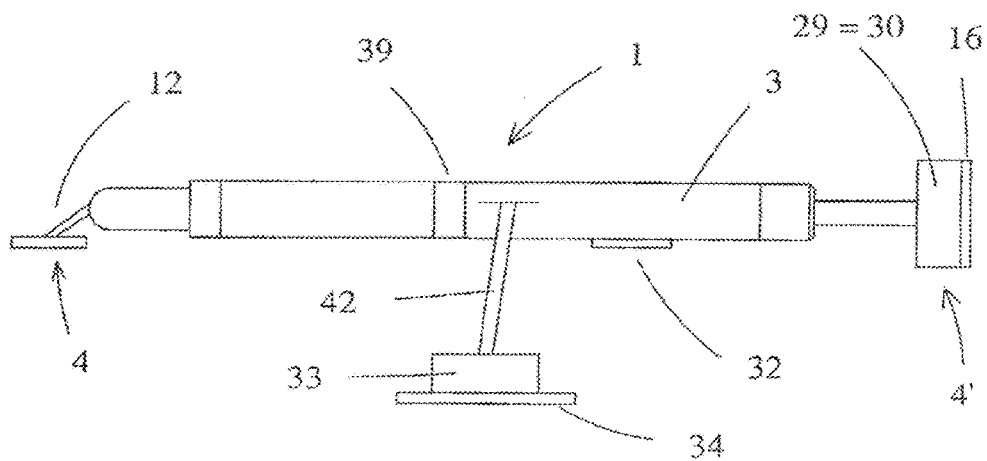
FIG. 5 represents a perspective view of the first unit forming part of the device for assessing sensitivity, object of the present invention, said first unit being in fully retracted position.

In FIG. 5 the first unit (1) can be seen, in which the Peltier cell with ventilators (16) and the vibration applicator (12) have been completely deployed. A support element (42) of the first unit (1) can also be seen, which couples to the casing (3) through a hole made in it, said element (42) having a rubber base (34) to prevent vibrations from the ground transmitting to the first unit (1). The first unit (1) may have temperature sensors, a skin sensor (29) and an ambient temperature sensor (30) that are incorporated on the thermoalgesic unit containing the Peltier cell with ventilators.

Figure 6:
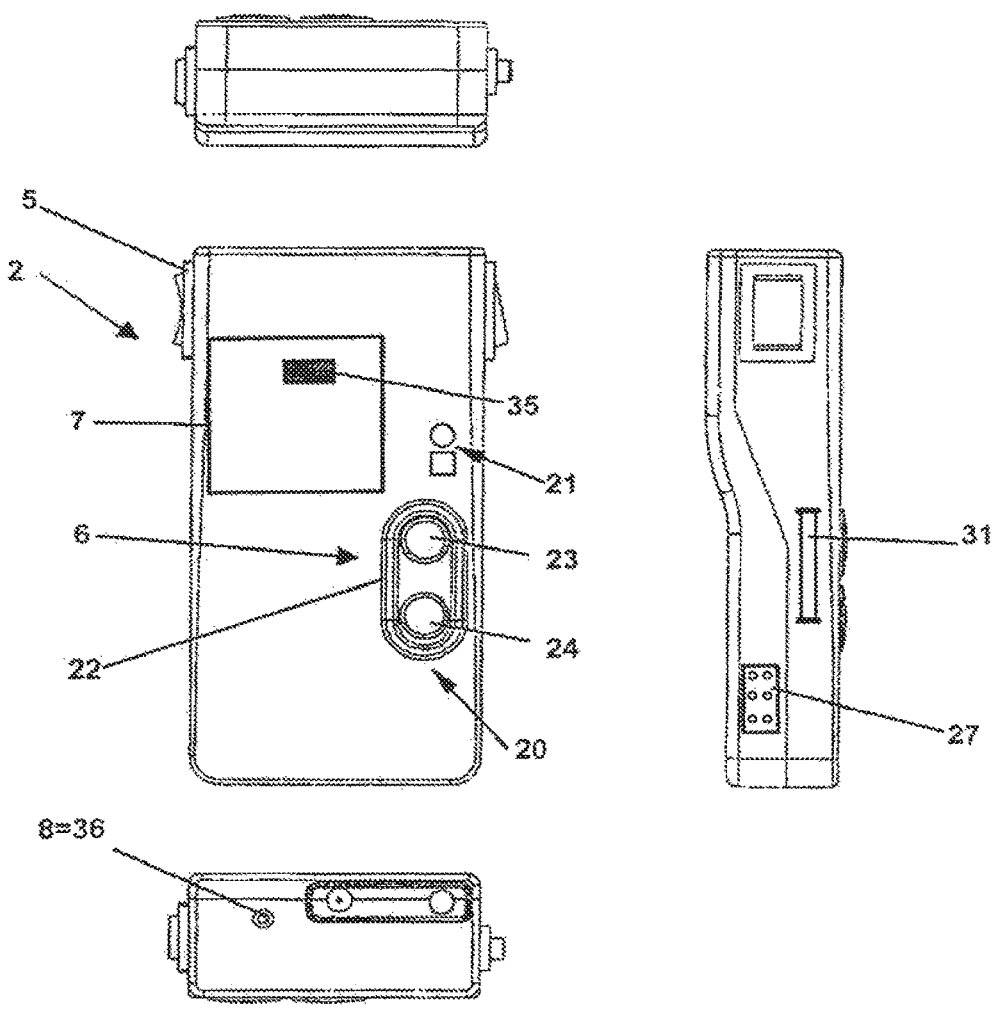
FIG. 6 represents a perspective view of the second unit forming part of the device for assessing sensitivity, object of the present invention.

In FIG. 6, the configuration of the second unit (2) is shown, which consists of means for data input (6), means for data display (7) and indicator means (8). The data input means are embodied in a button pad (20) that has a first area (21) of buttons comprising a button for the switching on and off and another area with two buttons for the input of data corresponding to the vibration generating means and for input of data corresponding to the means generating cold-heat, and a second area (22) of buttons having a first button (23) that will be pushed when the patient identifies a vibration and a second button (24) that will be pushed when the patient identifies none.

The main aim of the button pad is to register the detection of the different stimuli by the patient being assessed; thus the first button (23) corresponds to the capture of affirmative data (yes) regarding the identification of stimuli, while the second button (24) corresponds to the capture of negative data (no), or the lack of identification of the stimuli. Regarding the data display means (7), they comprise a screen (44) that can display at least the following data: the date and time when the assessment or test is carried out, the number and type of test being run, the score obtained in each test and in total, and the percentage of stimuli detected by the patient.

The indicator means (8) are several leds (36) red and green in colour, whereby the led will light up red when the stimulus is being applied by the unit (1); it will subsequently stop lighting up and the green colour led will light up, indicating that at that moment the patient may proceed to pushing the buttons of the second unit (2).

Additionally, the second unit (2) will have visual warning means (35) that may appear on the screen itself, and/or aural, which indicate the battery charge (33) of the unit is near exhaustion and also may warn about the test results if they exceed certain predetermined values. In addition, it may have a connection port (27) for the second unit (2) to a personal computer with the aim of processing the data collected by said unit if necessary. This unit (2) may have emergency batteries that will activate in the case the battery (33) is exhausted during the assessment process.

The Peltier cell with ventilators (16) will have a dimension of 5×2.5 cm$^2$, and the tuning fork (9) a working frequency of 125 to 248 Hz. The increases or decreases of the stimulation temperatures used for the Peltier cell with ventilators (16) consist of pre-established random ramps ranging from 9° (pyramidal scale) for cold, 45° for the feeling of heat, to a limit of 49° (trapezoid scale) for the feeling of thermal pain. Each stimulus is maintained for a period of 10 seconds and 3 stimuli are repeated in one same period, except for the pain resulting from only one stimulus.

The responses to the five sensorial parameters assessed (cold, heat, thermal pain and vibration), are, in turn, registered in the second unit (2). Each response (pulsation of the appropriate button) should be given after application of the corresponding stimulus with a decision time of 10 seconds. Thus, each test (cold, heat, thermal pain and vibration) should provide data from 3 responses assigned to 3 stimuli of the same type but of different intensity. The thermal pain stimulus is applied only on one occasion, so it throws up a response result.

The covering material of units (1) and (2) is hard (not flexible) plastic, similar to metal, in the same way as the internal structure, for external protection and protection of components.

According to the disclosed configuration of the device, the assessment procedure is carried out in the following way.

The first (1) and second (2) units are switched on.

A self-test is carried out of said units, testing among other data, the battery charge (33), the date and operational status of radiofrequency or infrared communications between both units.

Assessment Test for Sensitivity to Vibrations

Figure 15:
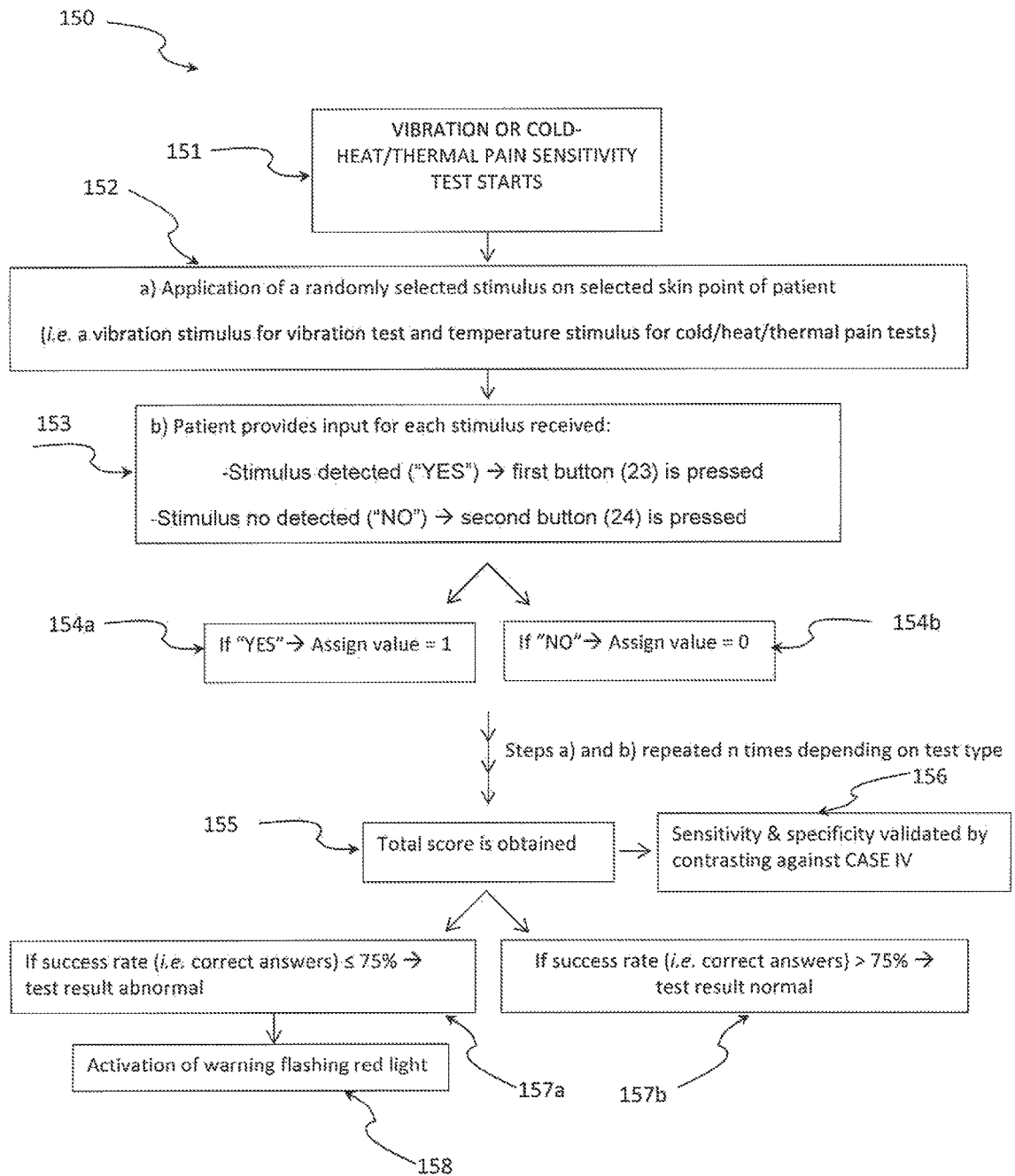

Reference is made to FIG. 15, an exemplary quantification programme for conducting Cold/Heat/Temperature or Vibration pain sensitivity test.

As shown, the Vibration pain sensitivity test starts at step 151. Turning the sleeve (39) of the first unit (1) clockwise (the sleeve may be optionally located on the distal end, corresponding to the vibrator outlet) while holding fixedly the shortest portion (38) of the casing (3), the vibrations applicator (12) is telescopically extracted from the first unit (1).

At step 152, the applicator (12) is placed in contact with the skin area just before the nail bed of the first toe of the right foot, then on the second toe, and continuing in the same way with the left foot. If necessary, one may proceed in the same way with the upper limbs. The contact between the surface of the applicator and the skin must be complete.

The insulating rubber plate is placed under the skin bed of each finger explored.

The vibration test session is initiated.

The complete examination of vibration stimuli is carried out, consisting of a total of 3 tests. Each test should generate 4 stimuli, i.e. a total of 12 stimuli and 12 responses.

The selected method for the assessment is: the "yes-no paradigm" ("two-interval forced choice", which has been included in the software installed in the units of the device).

The intensities of stimuli consist of: A) High intensity; B) intermediate intensity; C) low intensity, and D) null intensity. Each of these intensities is always characterized by presenting a vibration wave of sinusoidal form with a duration of 4 milliseconds and a wave width of +100 μm. a—100 μm (125 to 248 Hz) with a constant intensity for A) 5.77 μm, B) 2.38 μm, C) 1.19 μm, and D) 0.01 μm.

The mode in which each test is carried out by the software programme is selected randomly as regards intensity and order of application of each stimulus according to the pre-established values in A), B), C) and D).

The time duration of each stimulus is 1.8 s and the pause interval between each stimulus is 13 s.

The beginning of the test is signalled by the lighting up of a red-colour led (36) in the second unit (2), and then the response must be decided (pulsation of the buttons on the second unit (2) by the patient), as the green-colour led (36) of the second unit (2) lights up. If the patient does not press any button after a stimulus, the response is interpreted as missed and is not given a value.

The stimulation programmes indicated are used randomly and distributed in different intensity gradation scales in the successive tests, using the described alternatives and in all cases with 6 non-consecutive null stimuli, such as, for example:

| 1° | 2° | 3° | 4° |
|----|----|----|----|
| A  | D  | B  | D  |
| A  | D  | C  | D  |
| B  | D  | A  | D  |
| B  | D  | C  | D  |
| C  | D  | A  | D  |
| C  | D  | B  | D  |

At step 153, the patient must indicate to the second unit (2) the perception received of the stimulus. If the stimulus is identified, the affirmative (yes) button (23) will be pushed, and if the stimulus is not identified, the negative (no) button (24) will be pushed.

Each response is assessed in the quantification programme as:

Response 1 (shown at step 154a): success (stimulus detected by the patient).

Response 0 (shown at step 154b): error (stimulus not detected by the patient).

These results may be assessed in percentiles.

In steps 155 and 157a-b, the test result is deemed abnormal if the group of responses gives a success rate lower than 75%.

If more than two null stimuli are given positive responses by the patient, the programme enters self-suspension, indicating on screen that the test has failed and the need to start again; if the error persists, the software will not allow continuation with tests until 48 hours have elapsed (the time needed to consult the error with the distributor and/or healthcare personnel).

After completing the test, the result in percentage of correct responses is shown on the screen of the response unit. If the result is 75% or less, as shown in step 157a, a warning flashing red light will come on in step 158 (optionally a sound alarm), indicating that the test result is not normal.

The results may be transferred to a personal computer and represented in numeric and/or graphical form. With these values one can identify for each area explored the stage at which the implemented tests are.

Assessment Test for Sensitivity to Temperature

As shown, the COLD-HEAT/THERMAL pain sensitivity test starts at step 151. By turning the sleeve (39) (or the sleeve located on the end with the Peltier plate with ventilators) counterclockwise and fixedly holding the longest portion (37) of the casing (3), the temperature and thermal pain stimulator (Peltier cell with ventilators (16)) one wishes to use are deployed.

By using the sensors of the unit an ambient temperature measurement is made.

By means of the sensors of the unit, a skin surface temperature measurement is made.

A similar measurement is made for the vibration stimulus, quantifying the response capacity to the stimulus of the patient.

In this case, in step 156, the sensitivity and specificity of tests should be validated by contrasting against the method in CASE IV and with patient controls that are healthy or diseased, determining responses obtained according to sex, site explored, age and physical variables.

For a better understanding of the specification, the references used in drawings are listed below:
1. first unit
2. second unit
3. casing of first unit
4. vibration generating means of the first unit
4'. means generating cold-heat
5. on/off and control means of the first unit
6. data input means of the second unit
7. data display means of the second unit
8. indicator means of the second unit
9. tuning fork
10. arms of the tuning fork
11. central point of the tuning fork
12. vibration applicator
13. Teflon button
14. rubber washer
15. speaker of tuning fork—piezo-electrical element
16. Peltier cell with ventilators
17. rotational axis of Peltier cell
18. turning axis of the casing
19. ejecting arm
20. button pad
21. first area button pad
22. second area button pad
23. a first button
24. second button
27. port
29. skin temperature sensor
30. ambient temperature sensor
33. batteries first unit
34. base layer of rubber first unit
35. warning means of the second unit
36. leds indicator means of the second unit.
37. part of casing
38. part of casing
39. sleeve deployed
40. stem of the tuning fork
41. guides
42. support element

The invention claimed is:

1. Device for assessing thermoalgesic and vibratory sensitivity, comprising:
a first unit configured to apply to localized points of a patient a plurality of stimuli comprising vibrations and temperature changes,
a second unit for communicating with the first unit via wireless transmission,
wherein the first unit comprises:
an outer casing,
a tuning fork that has two arms converging on a central point for applying vibration and a Peltier cell with ventilators for generating cold-heat to apply a plurality of stimuli to localized points of the patient body,
an ejecting arm adapted to move respect to the outer casing in order to deploy the Peltier cell with ventilators, and
an electrical circuit adapted to vary the intensity of the plurality of stimuli comprising the vibration from the tuning fork and the cold-heat from the Peltier cell,
wherein the ventilators are configured to rotate around an axis perpendicular to an axis of the outer casing,
wherein the ejecting arm is disposed parallel to said axis and is connected to the outer casing to move with respect to the outer casing according to a direction parallel to the axis, in such a way that when the ejecting arm is:
in a deployed position, the ejecting arm and the Peltier cell with ventilators project from the outer casing and the Peltier cell with ventilators is configured to adopt an inclination with respect to the axis of the outer casing and with respect to an angle of the Peltier cell with ventilators when the ejecting arm is in a retracted position;
wherein the second unit comprises:
a power button, and
two buttons for the input of data to operate the tuning fork that has two arms and the Peltier with ventilators,
an indicator for indicating different operational stages of the first unit, and
wherein the device is adapted to execute a quantification programme to quantify a response capacity of the patient to the plurality of stimuli,
wherein said response capacity is based on a score derived from a group of responses to the plurality of stimuli;

wherein the response capacity is affirmative when at least one of the plurality of stimuli is detected by the patient or negative when the at least one of the plurality of stimuli is not detected by the patient, wherein the first and second units are configured to implement a self-test after the first and second units are turned on, said self-test comprising an assessment of a battery charge, an ambient temperature, a skin temperature, a radiofrequency or infrared communication status, wherein the first and second units are configured to be powered electrically and autonomously, wherein the outer casing comprises a rubber washer on a tip of the outer casing, wherein a piezo-electrical element of 125 to 248 Hz or a speaker with coil for generating the vibrations is fixed to a free end of each of the two arms of the tuning fork.

2. The device of claim 1, wherein the first unit comprises a skin temperature sensor and an ambient temperature sensor adapted to determine temperature to be able to carry out the assessment.

3. The device of claim 1, wherein the first unit remains coupled to the second unit through a slot made in the second unit and a projection that fits into said slot associated to the first unit, in such a way that both units are coupled to each other, forming the device.

4. The device of claim 1, wherein the first unit comprises a base configured to rest on the ground during use of the device and a rubber layer on the base.

5. The device claim 1, wherein the indicator comprises a plurality of LEDS of different colours including red and green, whereby the LED of red colour is configured to light up when the plurality of stimuli is being applied by the first unit and, the LED of green colour is configured to light up to indicate to the patient to push a first button when the patient identifies the vibration, or a second button configured to be pushed when the patient identifies no vibration.

6. The device of claim 1 wherein a screen configured to display at least the following data: date and time, a number and type of test being carried out, a score obtained in each test and in total, and a percentage of the plurality of stimuli detected by the patient.

7. The device of claim 1, wherein the device is portable.

8. The device claim 1, wherein the plurality of stimuli is applied during a vibration stimulation programme comprising a plurality of vibrations randomly selected from the group consisting of 5.77 µm, 2.38 µm, 1.19 µm and 0.01 µm.

9. The device of claim 8, wherein the quantification programme is configured to enter self-suspension when more than two vibrations of 0.01 pm are given affirmative responses by the patient, and then indication is given on a data display that the test has failed and the need to start, again, wherein said data display is a screen.

10. The device of claim 1, wherein the response results are assessed in percentiles and the test result is deemed abnormal when the group of responses gives an affirmative response of lower than 75%.

11. The device of claim 10 wherein, when a test result is deemed abnormal, a warning flashing red light will come on.

12. The device of claim 11, wherein when said test result is deemed abnormal, an alarm is sounded.

* * * * *

UNITED STATES PATENT AND TRADEMARK OFFICE
CERTIFICATE OF CORRECTION

PATENT NO. : 10,376,204 B2  
APPLICATION NO. : 13/262126  
DATED : August 13, 2019  
INVENTOR(S) : Ariel Andrés Odriozola Orlandi Page 1 of 1

It is certified that error appears in the above-identified patent and that said Letters Patent is hereby corrected as shown below:

On the Title Page

Item (30) Foreign Application Priority Data:
"200900890" should be changed to -- P200900890 --

Signed and Sealed this  
Nineteenth Day of November, 2019

Andrei Iancu  
*Director of the United States Patent and Trademark Office*